US010258998B2

United States Patent
Case et al.

(10) Patent No.: US 10,258,998 B2
(45) Date of Patent: Apr. 16, 2019

(54) OPTICAL MONITORING SYSTEM FOR BLOOD PROCESSING SYSTEM

(71) Applicant: Fenwal, Inc., Lake Zurich, IL (US)

(72) Inventors: Brian C. Case, Lake Villa, IL (US);
Steven R. Katz, Deerfield, IL (US);
William H. Cork, Mettawa, IL (US);
Jonathan Prendergast, Palatine, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 15/485,691

(22) Filed: Apr. 12, 2017

(65) Prior Publication Data
US 2017/0225177 A1    Aug. 10, 2017

Related U.S. Application Data

(63) Continuation of application No. 14/058,514, filed on Oct. 21, 2013, now Pat. No. 9,662,665, which is a (Continued)

(51) Int. Cl.
*B04B 5/04* (2006.01)
*A61M 1/02* (2006.01)
(Continued)

(52) U.S. Cl.
CPC ......... *B04B 5/0442* (2013.01); *A61M 1/0209* (2013.01); *A61M 1/3693* (2013.01);
(Continued)

(58) Field of Classification Search
CPC .............. A61M 1/3693; A61M 1/3696; A61M 1/0209; A61M 2205/3317;
(Continued)

(56) References Cited

U.S. PATENT DOCUMENTS

| 4,810,090 A | 3/1989 | Boucher et al. |
| 5,104,526 A | 4/1992 | Brown et al. |

(Continued)

FOREIGN PATENT DOCUMENTS

| EP | 0 771 569 A2 | 5/1997 |
| EP | 0 779 077 A1 | 6/1997 |

(Continued)

OTHER PUBLICATIONS

Extended European Search Report for European Patent Appl'n. No. 16191934.5, dated Jan. 23, 2017.

*Primary Examiner* — Timothy C Cleveland
(74) *Attorney, Agent, or Firm* — Cook Alex Ltd.

(57) ABSTRACT

An optical monitoring system is provided for use with a blood processing system. The system includes a light source configured to illuminate a disposable flow circuit received in a centrifuge and a light detector configured to receive an image of the disposable flow circuit. A controller combines two or more of the images received by the light detector to generate a two-dimensional output. The output is used to control the separation of blood within the disposable flow circuit. The monitoring system may also be used to verify that the disposable flow circuit is suitable for use with the centrifuge or that the disposable flow circuit is properly aligned within the centrifuge. The monitoring system may be positioned outside of the centrifuge bucket which receives the centrifuge.

8 Claims, 10 Drawing Sheets

Related U.S. Application Data continuation of application No. 14/112,969, filed as application No. PCT/US2012/056992 on Sep. 25, 2012, now Pat. No. 9,731,302.

(60) Provisional application No. 61/539,034, filed on Sep. 26, 2011.

(51) Int. Cl.
*A61M 1/36* (2006.01)
*B04B 13/00* (2006.01)

(52) U.S. Cl.
CPC ........... *A61M 1/3696* (2014.02); *B04B 13/00* (2013.01); *A61M 2205/12* (2013.01); *A61M 2205/14* (2013.01); *A61M 2205/18* (2013.01); *A61M 2205/276* (2013.01); *A61M 2205/331* (2013.01); *A61M 2205/3306* (2013.01); *A61M 2205/3313* (2013.01); *A61M 2205/3317* (2013.01); *A61M 2205/3331* (2013.01); *A61M 2205/6063* (2013.01); *A61M 2205/6072* (2013.01); *B04B 2005/045* (2013.01); *B04B 2005/0492* (2013.01); *B04B 2013/006* (2013.01)

(58) Field of Classification Search
CPC .... A61M 2205/331; A61M 2205/3306; A61M 2205/3313; B04B 5/0442; B04B 13/00
See application file for complete search history.

(56) References Cited

U.S. PATENT DOCUMENTS

| | | |
|---|---|---|
| 5,260,598 A | 11/1993 | Brass et al. |
| 5,298,476 A | 3/1994 | Hotta |
| 5,316,667 A | 5/1994 | Brown et al. |
| 5,868,696 A | 2/1999 | Giesler et al. |
| 6,254,784 B1 | 7/2001 | Nayak et al. |
| 7,327,443 B2 | 2/2008 | Scibona et al. |
| 7,355,685 B2 | 4/2008 | Scibona et al. |
| 7,422,693 B2 | 9/2008 | Carter et al. |
| 7,605,388 B2 | 10/2009 | Carter et al. |
| 7,951,059 B2 | 5/2011 | Sweat |
| 2004/0151633 A1 | 8/2004 | De Gaulle et al. |
| 2008/0041772 A1 | 2/2008 | Sweat et al. |
| 2011/0058070 A1 | 3/2011 | Awazu |
| 2011/0143905 A1 | 6/2011 | Kolenbrander et al. |

FOREIGN PATENT DOCUMENTS

| | | |
|---|---|---|
| WO | WO 96/40319 A1 | 12/1996 |
| WO | WO 03/000026 A2 | 1/2003 |
| WO | WO 03/026724 A1 | 4/2003 |
| WO | WO 2008/021633 A2 | 2/2008 |
| WO | WO 2008/114164 A1 | 9/2008 |

OPTICAL MONITORING SYSTEM FOR BLOOD PROCESSING SYSTEM

RELATED APPLICATION

This application is a continuation of U.S. patent application Ser. No. 14/058,514, filed Oct. 21, 2013, which is a continuation of U.S. patent application Ser. No. 14/112,969, filed Oct. 21, 2013, which is a U.S. national stage application of PCT Patent Application Serial No. PCT/US2012/056992, filed Sep. 25, 2012, which claims the benefit of and priority of U.S. Patent Application Ser. No. 61/539,034, filed Sep. 26, 2011, the contents of which are incorporated by reference herein.

DESCRIPTION

Technical Field

The disclosure relates to blood treatment systems and methods. More particularly, the disclosure relates to systems and methods for optically detecting the characteristics of a disposable flow circuit mounted within a durable blood separation system and the fluid flow therethrough.

BACKGROUND

Various blood processing systems now make it possible to collect particular blood constituents, rather than whole blood, from a blood source. Typically, in such systems, whole blood is drawn from a blood source, the particular blood component or constituent is separated, removed, and collected, and the remaining blood constituents are returned to the blood source. Removing only particular constituents is advantageous when the blood source is a human donor or patient, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents through centrifugation. This requires that the whole blood be passed through a centrifuge after it is withdrawn from, and before it is returned to, the blood source. To avoid contamination and possible infection (if the blood source is a human donor or patient), the blood is preferably contained within a sealed, sterile fluid flow system during the entire centrifugation process. Typical blood processing systems thus include a permanent, reusable assembly containing the hardware (centrifuge, drive system, pumps, valve actuators, programmable controller, and the like) that spins and pumps the blood, and a disposable, sealed, and sterile flow circuit that is mounted in cooperation on the hardware.

The centrifuge engages and spins the disposable flow circuit during a blood separation step. As the flow circuit is spun by the centrifuge, the heavier (greater specific gravity) components of the whole blood in the flow circuit, such as red blood cells, move radially outwardly away from the center of rotation toward the outer or "high-G" wall of the centrifuge. The lighter (lower specific gravity) components, such as plasma, migrate toward the inner or "low-G" wall of the centrifuge. Various ones of these components can be selectively removed from the whole blood by providing appropriately located channeling seals and outlet ports in the flow circuit. For example, in one blood separation procedure, plasma is separated from cellular blood components and collected, with the cellular blood components and a replacement fluid being returned to the blood source.

One disadvantage of known systems is that they may not include adequate safeguards to ensure that the proper disposable flow circuit is used and that the disposable flow circuit is properly aligned within the centrifuge. If an inappropriate flow circuit is used with the centrifuge (or if the flow circuit is improperly installed), damage can be done to the flow circuit and/or the centrifuge. Even if the flow circuit and centrifuge are not damaged, the blood may be improperly fractionated and processed, which reduces the effectiveness of the system and can even be harmful to a human connected to the system.

It is known to employ an optical sensor system to monitor the flow of blood and/or blood components through the flow circuit in the centrifuge and determine various characteristics of the flow. These optical sensor systems can be characterized as either one- or two-dimensional types. In comparison to known systems, it may be advantageous to provide an optical monitoring system with improved flow control functionality, additional functionality (beyond flow control), and/or alternative placement within a blood separation device.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, blood processing system is provided with a disposable flow circuit, a centrifuge, and a monitoring system. The disposable flow circuit is configured for the flow of whole blood and/or a separated blood component therethrough. The centrifuge is configured to receive at least a portion of the disposable flow circuit and separate at least one blood component from blood flowing through the disposable flow circuit. The monitoring system is configured to directly monitor the disposable flow circuit received by the centrifuge and includes a light source, a light detector, and a controller. The light source is configured to illuminate the portion of the disposable flow circuit received by the centrifuge. The light detector is configured to receive an image of the portion of the disposable flow circuit received by the centrifuge. The controller is configured to combine two or more of the images received by the light detector, generate a two-dimensional output, and control the separation of blood in the disposable flow circuit based at least in part on the output.

In another aspect, a method is provided for controlling a blood separation procedure. The method includes separating at least one blood component from blood in a centrifuge. Light is applied to the interior of the centrifuge and an image of the interior of the centrifuge is received. Two or more of the received images are combined and then a two-dimensional output is generated based, at least in part, on the images. The blood separation procedure is controlled based, at least in part, on the output.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
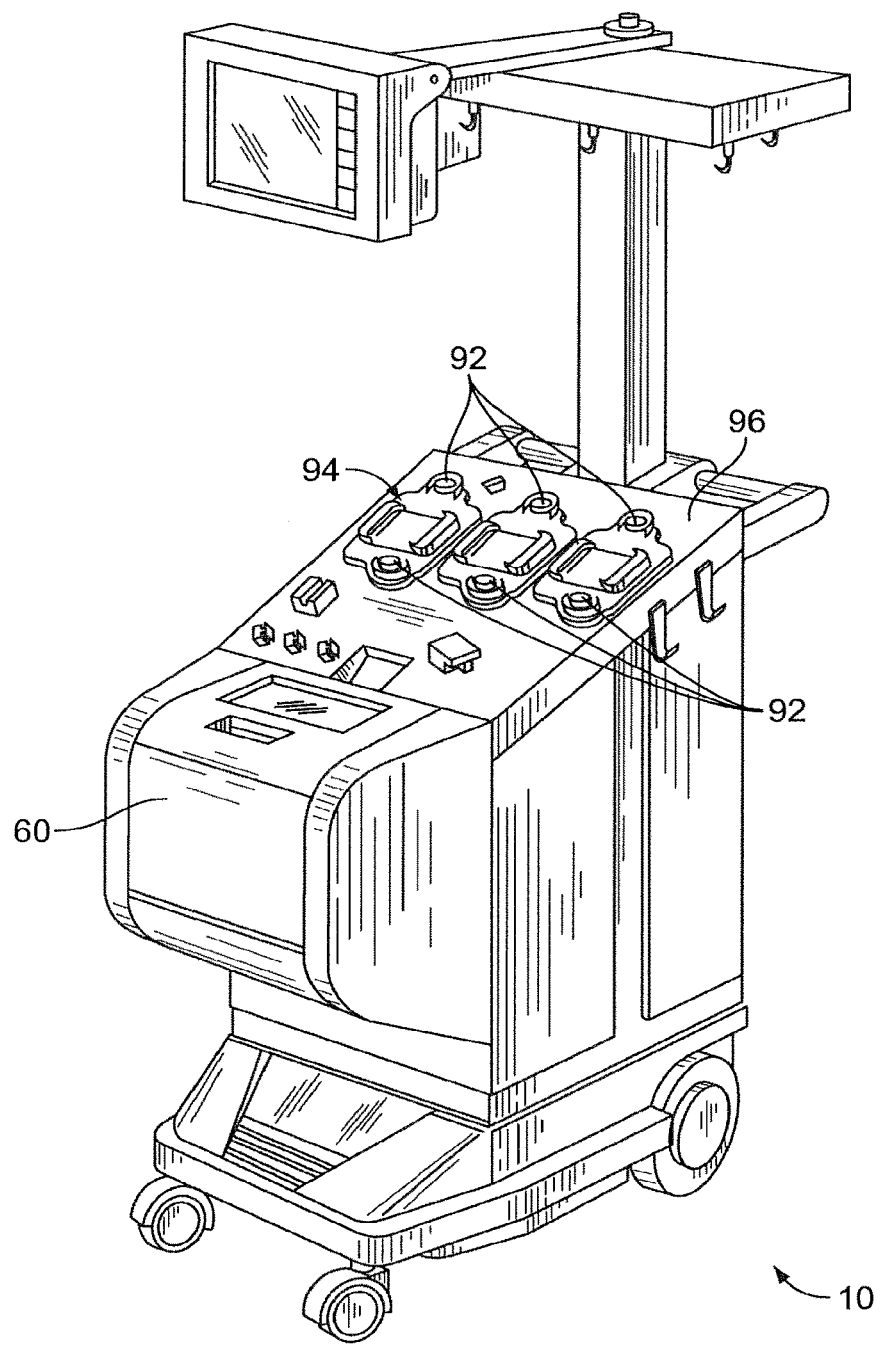
FIG. 1 is a perspective view of an exemplary blood separation device, in accordance with an aspect of the present disclosure.

Blood processing systems according to the present disclosure include a separation device, which may be variously provided without departing from the scope of the present disclosure. FIG. 1 shows an exemplary durable separation device 10 that may be employed in blood processing systems according to the present disclosure. The separation device 10 may be provided according to known design, such as the system currently marketed as the AMICUS® separator by Fenwal, Inc. of Lake Zurich, Ill., which is an affiliate of Fresenius Kabi AG of Bad Homburg, Germany, as described in greater detail in U.S. Pat. No. 5,868,696, which is hereby incorporated herein by reference. The separation device 10 can be used for processing various fluids, but is particularly well suited for processing whole blood and other suspensions of biological cellular materials. While fluid treatment principles will be described herein with reference to one particular system, it should be understood that these principles may be employed with other blood processing systems and separation devices without departing from the scope of the present disclosure.

Figure 2:
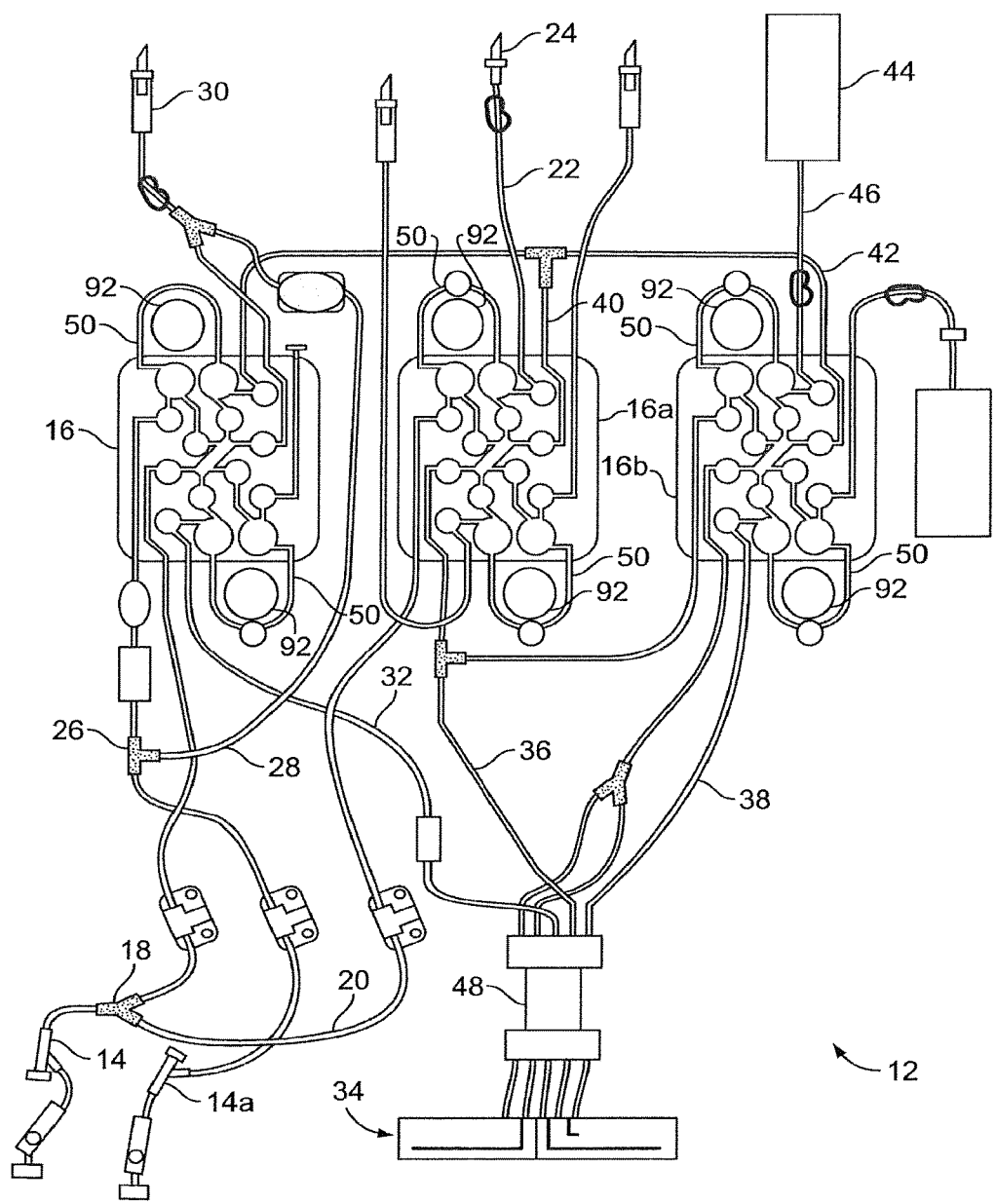
FIG. 2 is a diagrammatic view of an exemplary disposable flow circuit that may be used in combination with the separation device of FIG. 1.

FIG. 2 illustrates a disposable flow circuit 12 that may be used in combination with the separation device 10 of FIG. 1 to provide a blood processing system. The flow circuit 12 includes a variety of tubing and a number of components, only some of which will be described herein in greater detail. It should be understood that FIG. 2 illustrates only one example of a flow circuit which may be used in combination with the separation device 10 of FIG. 1 and differently configured flow circuits may also be employed without departing from the scope of the present disclosure.

The illustrated flow circuit 12 is a "two needle" system, which includes a pair of blood source access devices 14 and 14a (e.g., phlebotomy needles) for fluidly connecting a blood source with the flow circuit 12. The blood source access devices 14 and 14a are connected by tubing to a left cassette 16, which will be described in greater detail herein. One of the blood source access devices 14 is used to draw blood from the blood source into the flow circuit 12 and is connected to the left cassette 16 by a y-connector 18. The other leg of the y-connector 18 is connected to tubing 20 which leads to a middle cassette 16a. The tubing 20 is connected, through the middle cassette 16a, to additional tubing 22, which includes a container access device 24 (e.g., a sharpened cannula or spike connector) for accessing the interior of an anticoagulant container (not illustrated). During a blood treatment operation, anticoagulant from the anticoagulant container may be added to the blood from the blood source at the y-connector 18 prior to entering the left cassette 16.

The other blood source access device 14a is used to deliver or return blood, a blood component, and/or some other replacement fluid to the blood source and is also connected to the left cassette 16 by a y-connector 26. The other leg of the y-connector 26 is connected to tubing 28 connected at its other end to a container access device 30. Although not illustrated, the container access device 30 may be associated with a container having an amount of fluid (e.g., saline) to be used to prime the flow circuit 12 and/or delivered to the blood source via the blood source access device 14a.

The left cassette 16 also includes tubing 32 which is connected to a blood separation chamber 34 of the flow circuit 12 for flowing anticoagulated blood thereto. The blood separation chamber 34 separates the blood into its constituent parts (as will be described in greater detail herein) and returns the blood components to the flow circuit 12. In one embodiment, cellular blood components are returned to the middle cassette 16a of the flow circuit 12 from the blood separation chamber 34 via tubing 36, while substantially cell-free plasma is returned to a right cassette 16b of the flow circuit 12 from the blood separation chamber 34 via tubing 38. The cellular blood components may be pumped to the left cassette 16 via tubing 40, where they are returned to the blood source. The plasma may be pumped back to the left cassette 16 via tubing 42 for return to the blood source and/or it may be pumped into a container 44 via different tubing 46. The destination of the plasma (and the other fluids passing through the cassettes) depends upon the actuation of the various valves of the cassettes, as will be described in greater detail herein. The various tubing connected to the blood separation chamber 34 are bundled in an umbilicus 48, which will be described in greater detail herein.

Additional tubing may be connected from one port of a cassette to another port of the same cassette, so as to form tubing loops 50 which interact with a fluid flow element or pump to flow fluid through the flow circuit 12, as will be described in greater detail herein.

A. The Centrifuge

The separation device 10 includes a centrifuge 52 (FIGS. 3 and 4) used to centrifugally separate blood components. The separation device 10 may be programmed to separate blood into a variety of components (e.g., platelet-rich plasma and red cells). For illustrative purposes, a therapeutic plasma exchange procedure, in which the centrifuge 52 separates whole blood into cellular components and cell fragments (e.g., red blood cells and platelets) and substantially cell-free plasma, will be described herein. However, the principles described and claimed herein may be employed with other blood separation procedures without departing from the scope of the present disclosure.

Figure 3:
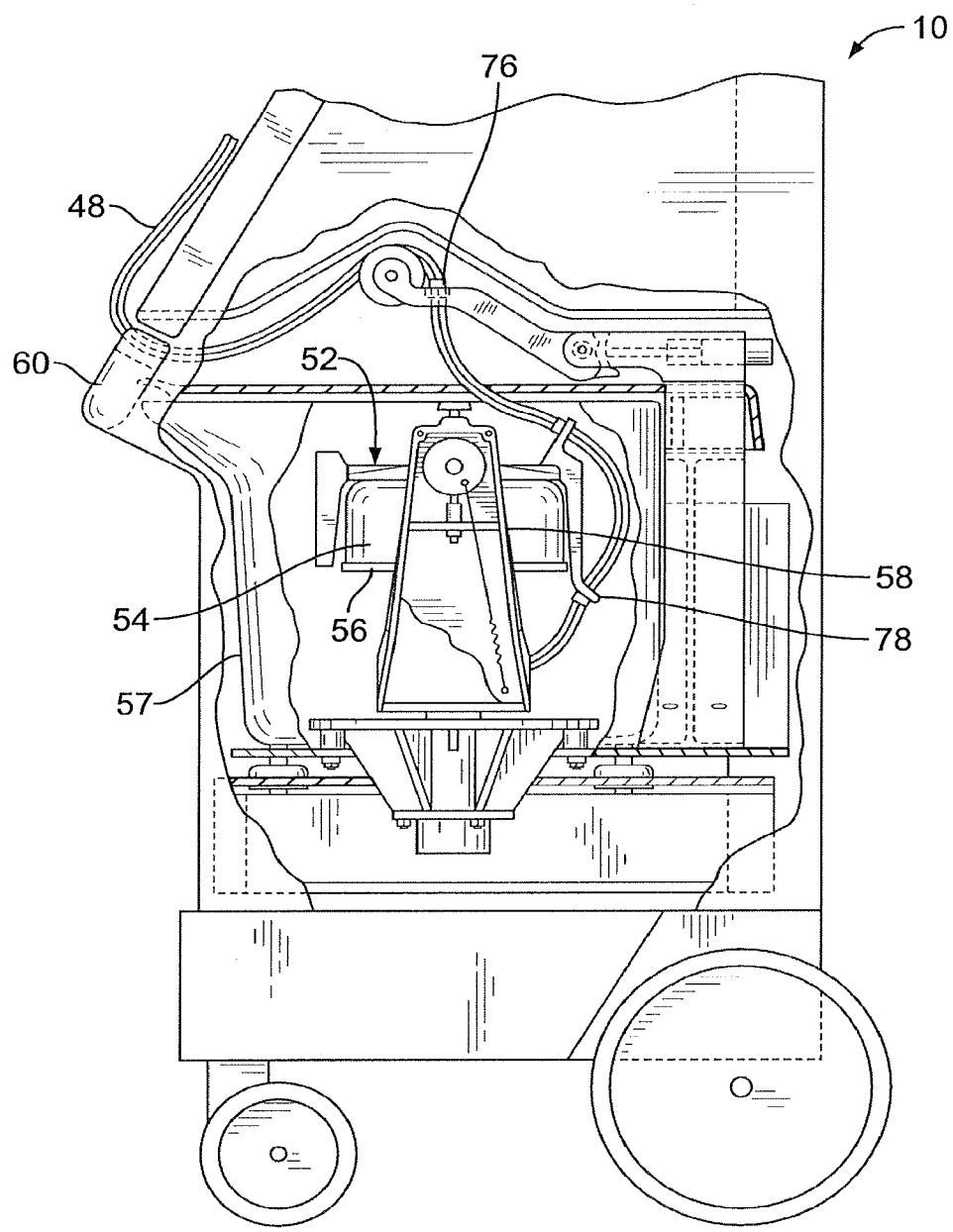
FIG. 3 is a side elevational view, with portions broken away and in section, of the separation device of FIG. 1, with a centrifuge bowl and spool of the system being shown in their operating position.
Figure 4:
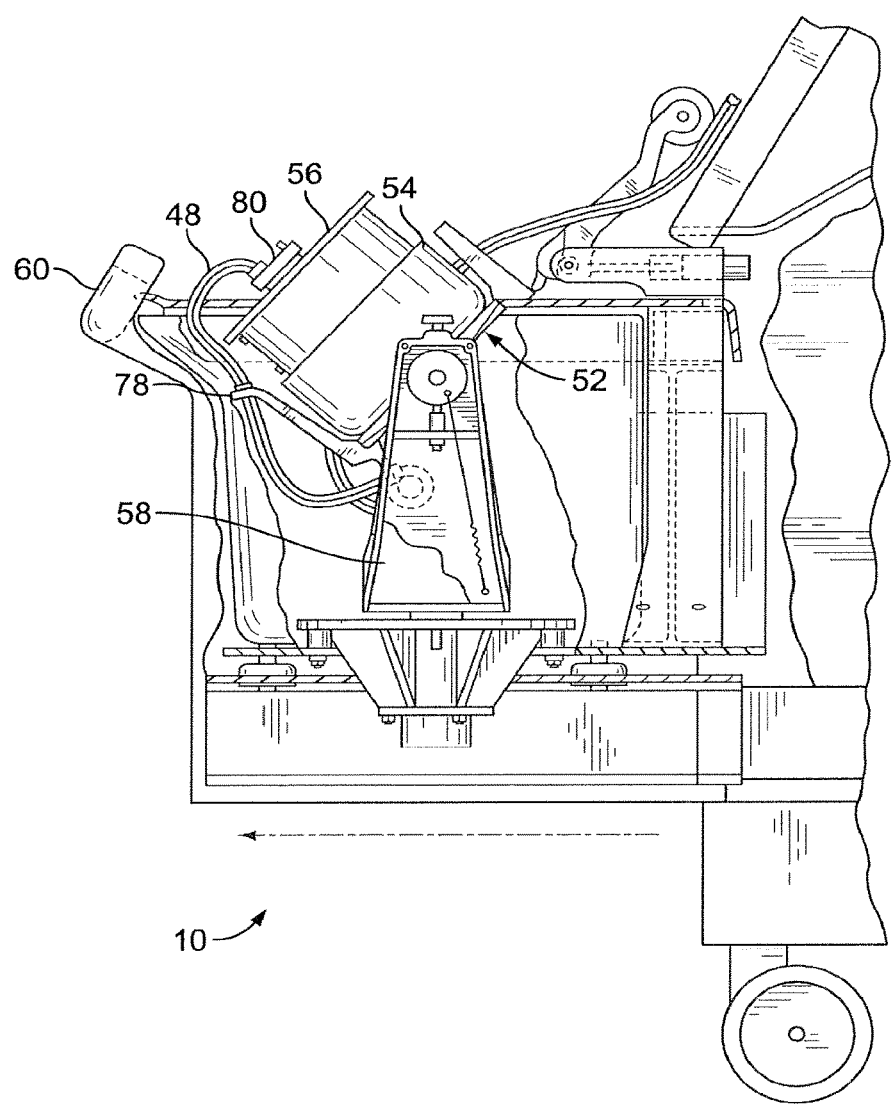
FIG. 4 is a side elevational view, with portions broken away and in section, of the separation device of FIG. 1, with the centrifuge bowl and spool shown in an upright position for receiving a blood separation chamber.

The illustrated centrifuge 52 is of the type shown in U.S. Pat. No. 5,316,667 to Brown et al., which is incorporated herein by reference. The centrifuge 52 comprises a bowl 54 and a spool 56 which are received within a bucket 57. The bowl 54 and spool 56 are pivoted on a yoke 58 between an operating position (FIG. 3) and a loading/unloading position (FIG. 4). The centrifuge 52 is housed within the bucket 57 in the interior of the separation device 10, so a door 60 is provided to allow access to the centrifuge 52 for loading and unloading the blood separation chamber 34, as will be described in greater detail herein. The door 60 remains closed during operation to protect and enclose the centrifuge 52.

When in the loading/unloading position, the spool 56 can be opened by movement at least partially out of the bowl 54, as FIG. 4 shows. In this position, the operator wraps the flexible blood separation chamber 34 about the spool 56 (see FIG. 5). Closure of the spool 56 and bowl 54 encloses the chamber 34 for processing. When closed, the spool 56 and bowl 54 are pivoted into the operating position of FIG. 3 for rotation about an axis.

B. The Blood Separation Chamber

Figure 6:
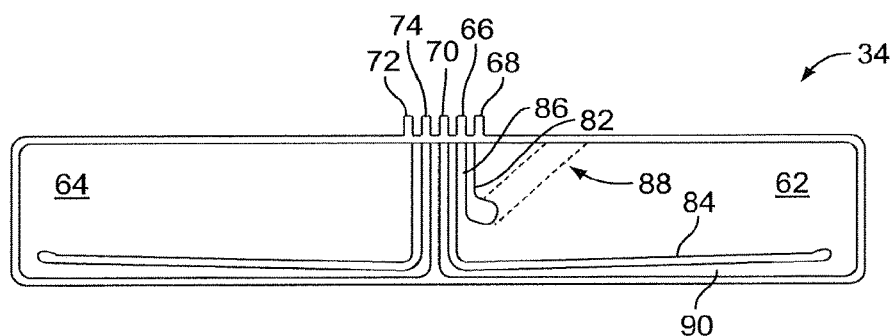
FIG. 6 is a plan view of the blood separation chamber of FIG. 5, out of association with the spool.

FIG. 6 shows a representative embodiment of a blood separation chamber 34 which may be used in connection with the present disclosure. The chamber 34 shown in FIG. 6 allows for either single- or multi-stage processing. When used for multi-stage processing, a first stage 62 separates whole blood into first and second components. Depending on the nature of the separation procedure, one of the components may be transferred into a second stage 64 for further processing.

Figure 5:
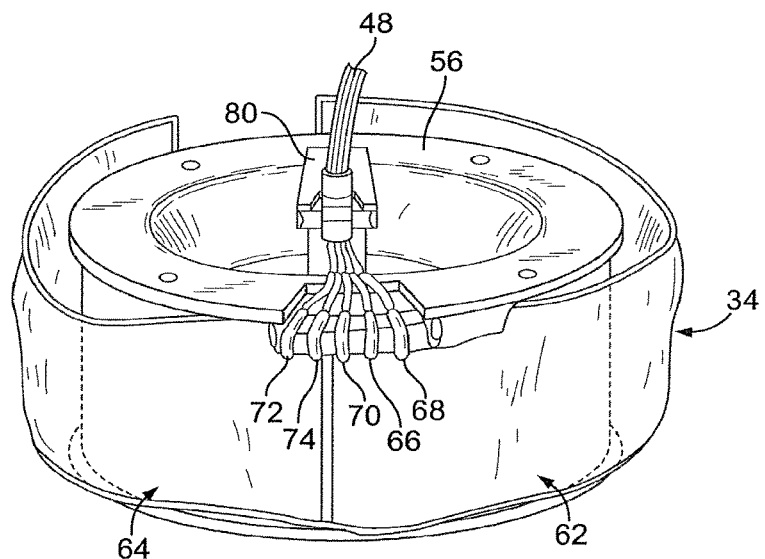
FIG. 5 is a top perspective view of the centrifuge spool of FIG. 4 in its upright position and carrying the blood separation chamber of the flow circuit of FIG. 2.

As FIGS. 5 and 6 best show, there are three ports 66, 68, and 70 associated with the first stage 62. Depending on the particular blood processing procedure, the ports may have different functionality. For example, in a therapeutic plasma exchange procedure, the port identified at 70 is used for conveying blood from a blood source into the first stage 62 (via tubing 32 of the flow circuit 12). During such a therapeutic plasma exchange procedure, the other two ports 66 and 68 serve as outlet ports for passing separated blood components from the first stage 62 to the flow circuit 12 (via tubing 36 and 38, respectively). More particularly, the first outlet port 68 conveys a low density blood component from the first stage 62, while the second outlet port 66 conveys a high density blood component from the first stage 62.

In a method of carrying out single-stage processing, one of the separated components is returned to the blood source, while the other is removed from the first stage 62 for further processing via an adsorption device (not illustrated). For example, when carrying out a therapeutic plasma exchange procedure, whole blood in the first stage 62 is separated into cellular components (i.e., a high density component) and substantially cell-free plasma (i.e., a low density component). The plasma is removed from the first stage 62 via the first outlet port 68 for further processing by the adsorption device, while the cellular components are removed from the first stage 62 via the second outlet port 66 and returned to the blood source. After the plasma has been treated by the adsorption device, it may be returned to the blood source.

If multi-stage processing is required, one of the components will be transferred from the first stage 62 to the second stage 64 via a port 72 associated with the second stage 64. The component transferred to the second stage 64 is further fractionated into sub-components, with one of the sub-components being removed from the second stage 64 via an outlet port 74 and the other sub-component remaining in the second stage 64. In the illustrated embodiment, the ports 66, 68, 70, 72, and 74 are arranged side-by-side along the top transverse edge of the chamber 34.

While the same ports 66, 68, and 70 of the first stage 62 are used as in the above-described therapeutic plasma exchange procedure, the ports 66 and 70 have different functionality in a multi-stage separation procedure. In one method of multi-stage operation, such as platelet collection, blood enters the first stage 62 via the port 66 and is separated into red blood cells (i.e., the high density blood component) and platelet-rich plasma (i.e., the low density blood component). The red blood cells are returned to the blood source (via the port 70), while the platelet-rich plasma is conveyed out of the first stage 62 (via the first outlet port 68) and into the second stage 64 (via the inlet port 72). In the second stage 64, the platelet-rich plasma is separated into platelet-poor plasma and platelet concentrate. The platelet-poor plasma is removed from the second stage 64 (via the outlet port 74), leaving platelet concentrate in the second stage 64 for resuspension and transfer to one or more storage containers.

As best shown in FIG. 5, the tubing umbilicus 48 of the flow circuit 12 is attached to the ports 66, 68, 70, 72, and 74. The umbilicus 48 interconnects the first and second stages 62 and 64 with each other and with the components of the flow circuit 12 positioned outside of the centrifuge 52. As FIG. 3 shows, a non-rotating (zero omega) holder 76 holds the upper portion of the umbilicus 48 in a non-rotating position above the spool 56 and bowl 54. A holder 78 on the yoke 58 rotates the mid-portion of the umbilicus 48 at a first (one omega) speed about the suspended spool 56 and bowl 54. Another holder 80 (FIGS. 4 and 5) rotates the lower end of the umbilicus 48 at a second speed twice the one omega speed (the two omega speed), at which speed the spool 56 and bowl 54 also rotate. This known relative rotation of the umbilicus 48 keeps it untwisted, in this way avoiding the need for rotating seals.

As FIG. 6 shows, a first interior seal 82 is located between the low density outlet port 68 and the high density outlet port 66. A second interior seal 84 is located between the high density outlet port 66 and the blood inlet port 70. The interior seals 82 and 84 form a fluid passage 86 (an outlet for high density blood components in a therapeutic plasma exchange procedure) and a low density collection region 88 in the first stage 62. The second seal 84 also forms a fluid passage 90 (a blood inlet in a therapeutic plasma exchange procedure) in the first stage 62.

C. The Cassettes

Blood entering the blood separation chamber 34 is pumped thereinto by one or more pumps 92 of the separation device 10 (FIGS. 1 and 2) acting upon one or more of the tubing loops 50 extending from the cassettes 16-16b of the flow circuit 12 (FIG. 2). An exemplary cassette 16 is illustrated in greater detail in FIGS. 7 and 8, while the pumps 92 and associated cassette holder 94 are shown in greater detail in FIG. 9.

Before beginning a given blood processing and collection procedure, the operator loads various components of the flow circuit 12 onto the sloped front panel 96 and centrifuge 52 of the separation device 10. As described above, the blood separation chamber 34 and the umbilicus 48 of the flow circuit 12 are loaded into the centrifuge 52, with a portion of the umbilicus 48 extending outside of the interior of the separation device 10, as shown in FIG. 3. The sloped front panel 96 of the separation device 10 includes at least one cassette holder 94 (three in the illustrated embodiment), each of which is configured to receive and grip an associated cassette 16-16b of the flow circuit 12.

Figure 7:
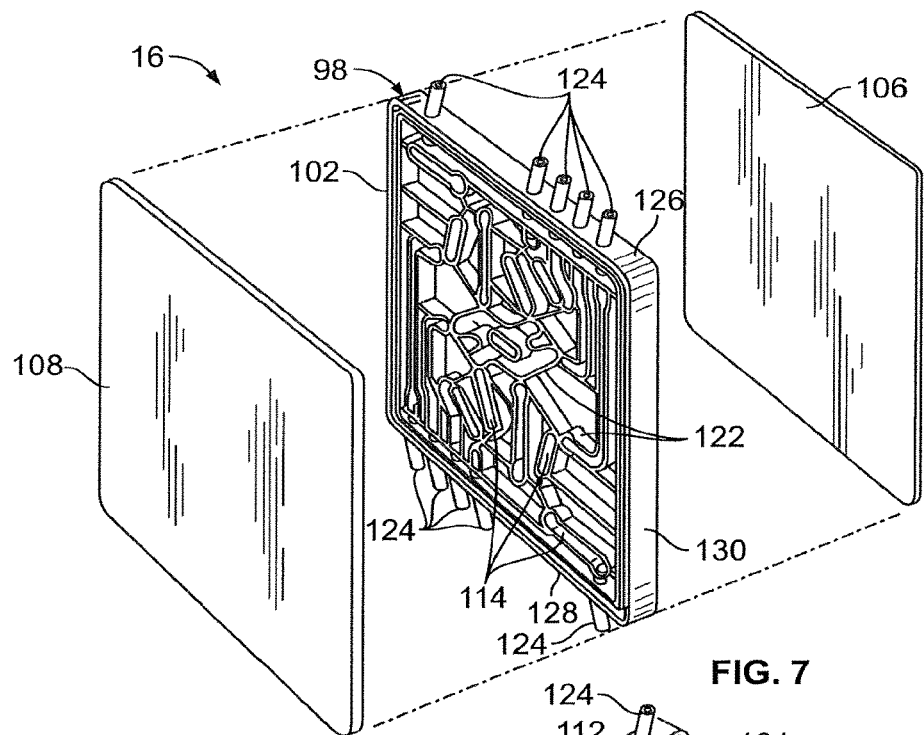
FIG. 7 is an exploded perspective view of a fluid processing cassette of the flow circuit of FIG. 2.
Figure 8:
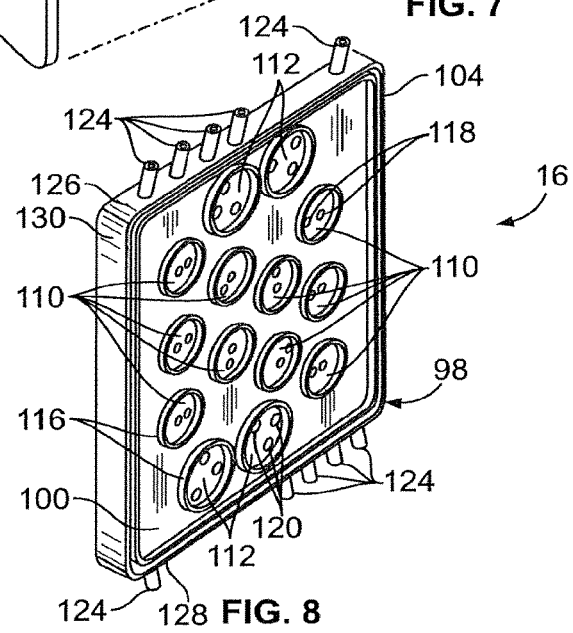
FIG. 8 is a perspective view of an underside of the fluid processing cassette of FIG. 7.
Figure 9:
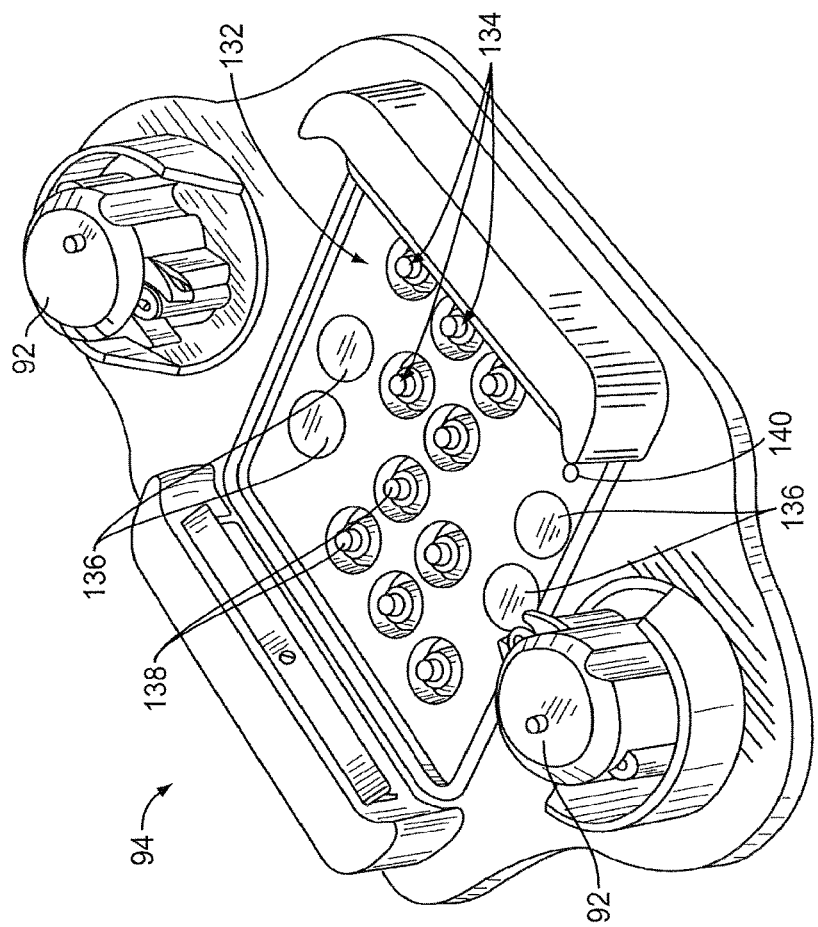
FIG. 9 is a perspective view of a cassette holder of the blood processing system of FIG. 1.

Each cassette 16-16b, one of which is shown in FIGS. 7 and 8, includes an injection molded body 98 that is compartmentalized by an interior wall 100 (FIG. 8) to present or form a topside 102 (FIG. 7) and an underside 104 (FIG. 8). For the purposes of description, the topside 102 is the side of the cassette 16 that, in use, faces away from the separation device 10, while the underside 104 faces towards the separation device 10. A flexible diaphragm 106 overlies and peripherally seals the underside 104 of the cassette 16. A generally rigid upper panel 108 overlies the topside 102 of the cassette 16 and is sealed peripherally and to the raised channel-defining walls in the cassette 16, as described later.

In one embodiment, the cassette 16, the interior wall 100, and the upper panel 108 are made of a rigid medical grade plastic material, while the diaphragm 106 is made of a flexible sheet of medical grade plastic. The upper panel 108 and the diaphragm 106 are sealed about their peripheries to the peripheral edges of the top- and undersides 102, 104 of the cassette 16, respectively.

As shown in FIGS. 7 and 8, the top- and undersides 102, 104 of the cassette 16 contain preformed cavities. On the underside 104 of the cassette 16 (FIG. 8), the cavities form an array of valve stations 110 and an array of pressure sensing stations 112. On the topside 102 of the cassette 16 (FIG. 7), the cavities form an array of channels or paths 114 for conveying liquids. The valve stations 110 communicate with the liquid paths 114 through the interior wall 100 to interconnect them in a predetermined manner. The sensing stations 112 also communicate with the liquid paths 114 through the interior wall 100 to sense pressures in selected regions. The number and arrangement of the liquid paths 114, the valve stations 110, and the sensing stations 112 can vary but, in the illustrated embodiment, the cassette 16 provides nineteen liquid paths 114, ten valve stations 110, and four sensing stations 112.

The valve and sensing stations 110, 112 resemble shallow wells open on the cassette underside 104 (FIG. 8). Upstanding edges 116 rise from the interior wall 100 and peripherally surround the valve and sensing stations 110, 112. The valve stations 110 are closed by the interior wall 100 on the topside 102 of the cassette 16, except that each valve station 110 includes a pair of through holes or ports 118 in the interior wall 100. The ports 118 each open into selected different liquid paths 114 on the topside 102 of the cassette 16.

The sensing stations 112 are likewise closed by the interior wall 100 on the topside 102 of the cassette 16, except that each sensing station 112 includes three through holes or ports 120 in the interior wall 100 (FIG. 8). The ports 120 open into selected liquid paths 114 on the topside 102 of the cassette 16. These ports 120 channel liquid flow among the selected liquid paths 114 through the associated sensing station 112.

In one embodiment, the flexible diaphragm 106 overlying the underside 104 of the cassette 16 is sealed by ultrasonic welding to the upstanding peripheral edges 116 of the valve and sensing stations 110, 112. This isolates the valve stations 110 and sensing stations 112 from each other and the rest of the system. In an alternative embodiment, the flexible diaphragm 106 can be seated against the upstanding edges 116 by an external positive force applied by the cassette holder 94 against the diaphragm 106. The positive force, like the ultrasonic weld, peripherally seals the valve and sensing stations 110, 112.

The localized application of additional positive force (referred to herein as a "closing force") upon the intermediate region of the diaphragm 106 overlying a valve station 110 serves to flex the diaphragm 106 into the valve station 110. Such closing force is provided by the cassette holder 94, as will be described in greater detail herein. The diaphragm 106 seats against one of the ports 118 to seal the port 118, which closes the valve station 110 to liquid flow. Upon removal of the closing force, fluid pressure within the valve station 110, the application of a vacuum to the outer surface of the diaphragm 106, and/or the plastic memory of the diaphragm 106 itself unseats the diaphragm 106 from the port 118, opening the valve station 110 to liquid flow.

Upstanding channel sides or edges 122 rise from the interior wall 100 to peripherally surround and define the liquid paths 114, which are open on the topside 102 of the cassette 16. The liquid paths 114 are closed by the interior wall 100 on the underside 104 of the cassette 16, except for the ports 118, 120 of the valve and sensing stations 110, 112 (FIG. 8). The rigid panel 108 overlying the topside 102 of the cassette 16 is sealed by ultrasonic welding to the upstanding peripheral edges 122, sealing the liquid paths 114 from each other and the rest of the system.

In the illustrated embodiment, ten pre-molded tube connectors 124 extend out along opposite side edges 126, 128 of each cassette 16. The tube connectors 124 are arranged five on one side edge 126 and five on the other side edge 128. The other side edges 130 of the cassette 16, as illustrated, are free of tube connectors. The tube connectors 124 are associated with external tubing (FIG. 2) to associate the cassettes 16 with the remainder of the flow circuit 12, as described above.

The tube connectors 124 communicate with various interior liquid paths 114, which constitute the liquid paths of the cassette 16 through which a fluid enters or exits the cassette 16. The remaining interior liquid paths 114 of the cassette 16 constitute branch paths that link the liquid paths 114 associated with the tube connectors 124 to each other through the valve stations 110 and sensing stations 112.

D. The Cassette Holders And Pumps

Turning now to the cassette holders 94 (FIG. 9), each receives and grips one of the cassettes 16-16b along the two opposed sides edges 130 in the desired operating position. The cassette holder 94 includes a pair of peristaltic pump stations 92. When the cassette 16 is gripped by the cassette holder 94, tubing loops 50 extending from the cassette 16 (FIG. 2) make operative engagement with the pump stations 92. The pump stations 92 are operated to cause fluid flow through the cassette 16.

The flexible diaphragm 106 covering the underside 104 of the cassette 16 is urged into intimate contact with a valve and sensor array or assembly 132 by the cassette holder 94. The valve assembly 132 acts in concert with the valve stations 110 and sensing stations 112 of the cassette 16. The valve assembly 132 illustrated in FIG. 9 includes ten valve actuators 134 and four pressure sensing transducers 136. The valve actuators 134 and the pressure sensing transducers 136 are mutually arranged in the same layout as the valve stations 110 and sensing stations 112 on the underside 104 of the cassette 16. When the cassette 16 is gripped by the cassette holder 94, the valve actuators 134 align with the cassette valve stations 110. At the same time, the pressure sensing transducers 136 mutually align with the cassette sensing stations 112.

In one embodiment, each valve actuator 134 includes an electrically actuated solenoid pin or piston 138. Each piston 138 is independently movable between an extended position and a retracted position. When in its extended position, the piston 138 presses against the region of the diaphragm 106 that overlies the associated valve station 110. In this position, the piston 138 flexes the diaphragm 106 into the associated valve station 110, thereby sealing the associated valve port 118. This closes the valve station 110 to liquid flow. When in its retracted position, the piston 138 does not apply force against the diaphragm 106. As before described, the plastic memory of the diaphragm 106 may be such that the removal of force is sufficient for the diaphragm to unseats from the valve port 118, thereby opening the valve station 110 to liquid flow. Alternatively, a vacuum may be applied to the diaphragm 106, for example by the vacuum port 140 illustrated in FIG. 9, to actively unseat the diaphragm 106 from the valve port 118.

The pressure sensing transducers 136 sense liquid pressures in the sensing stations 112 of the cassette 16. The sensed pressures are transmitted to a controller of the separation device 10 as part of its overall system monitoring function. If provided, the vacuum port 140 of the cassette holder 94 may provide suction to the diaphragm 106 of the cassette 16, drawing it into close contact with the transducers 136 for more accurate pressure readings.

E. Blood Separation

As described above, the centrifuge 52 rotates the blood separation chamber 34, thereby centrifugally separating whole blood received from a blood source into component parts, e.g., red blood cells, plasma, and buffy coat comprising platelets and leukocytes.

Figure 10:
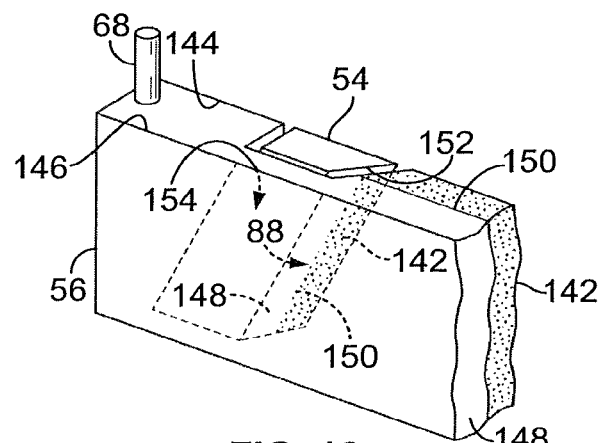
FIG. 10 is an enlarged perspective view of an interface ramp carried by the centrifuge in association with the blood separation chamber, showing the centrifugally separated red blood cell layer, plasma layer, and interface within the chamber when in a desired location on the ramp.

By way of example, in a therapeutic plasma exchange procedure, the fluid passage 90 channels blood directly into the circumferential flow path immediately next to the low density collection region 88. As shown in FIG. 10, the blood separates into an optically dense layer 142 containing cellular components, which forms as cellular components move under the influence of centrifugal force toward the high-G (outer) wall 144. The optically dense layer 142 will include red blood cells (and, hence, will be referred to herein as the "RBC layer") but, depending on the speed at which the centrifuge 52 is spun, other cellular components (e.g., larger white blood cells and platelets) may also be present in the RBC layer 142.

The movement of the component(s) of the RBC layer 142 displaces less dense blood components radially toward the low-G (inner) wall 146, forming a second, less optically dense layer 148. The less optically dense layer 148 includes plasma (and, hence, will be referred to herein as the "plasma layer") but, depending on the speed at which the centrifuge 52 is rotated and the length of time that the blood is resident in the centrifuge, other components (e.g., platelets and smaller white blood cells) may also be present in the plasma layer 148.

The transition between the formed cellular blood components and the liquid plasma component is generally referred to as the interface 150 (FIG. 10). Platelets and white blood cells (which have a density greater than plasma and usually less than red blood cells) typically occupy this transition region, although that also varies with centrifuge speed and residence time, as is well known in the technical field.

Figure 11:
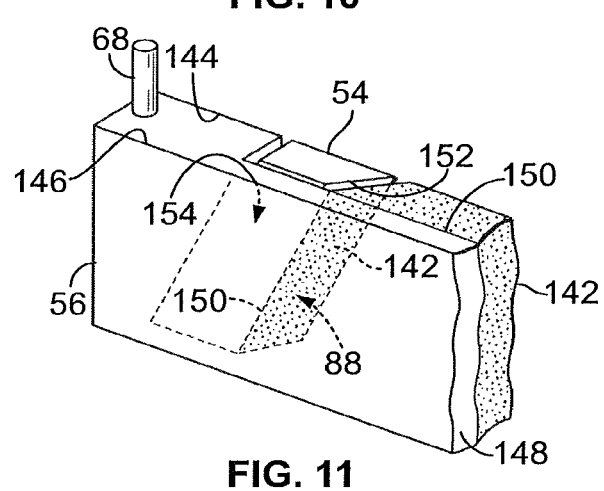
FIG. 11 is an enlarged perspective view of the interface ramp shown in FIG. 10, showing the red blood cell layer and interface at an undesired high location on the ramp.
Figure 12:
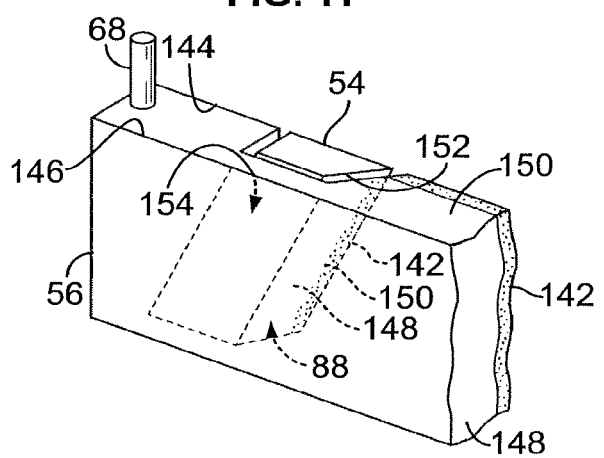
FIG. 12 is an enlarged perspective view of the interface ramp shown in FIG. 10, showing the red blood cell layer and interface at an undesired low location on the ramp.

The location of the interface 150 within the chamber 34 can dynamically shift during blood processing, as FIGS. 11 and 12 show. If the location of the interface 150 is too high (that is, if it is too close to the low-G wall 146 and the removal port 68, as FIG. 11 shows), cellular components can spill over and into the low density collection region 88, adversely affecting the quality of the low density components (typically plasma). On the other hand, if the location of the interface 150 is too low (that is, if it resides too far away from the low-G wall 146, as FIG. 12 shows), the collection efficiency of the separation device 10 may be impaired.

As FIG. 10 shows, a ramp 152 extends from the high-G wall 144 of the bowl 54 at an angle across the low density collection region 88. The angle, measured with respect to the axis of the first outlet port 68 is about 30° in one embodiment. FIG. 10 shows the orientation of the ramp 88 when viewed from the low-G wall 146 of the spool 56. FIG. 6 shows, in phantom lines, the orientation of the ramp 152 when viewed from the high-G wall 144 of the bowl 54.

Further details of the angled relationship of the ramp 152 and the first outlet port 68 can be found in U.S. Pat. No. 5,632,893 to Brown et al., which is incorporated herein by reference.

The ramp 152 forms a tapered wedge that restricts the flow of fluid toward the first outlet port 68. The top edge of the ramp 152 extends to form a constricted passage 154 along the low-G wall 146. The plasma layer 148 must flow through the constricted passage 154 to reach the first outlet port 68.

As FIG. 10 shows, the ramp 152 makes the interface 150 between the RBC layer 142 and the plasma layer 148 more discernible for detection, displaying the RBC layer 142, plasma layer 148, and interface 150 for viewing through the high-G wall 144 of the chamber 34.

Further details of the separation chamber 34 and its operation may be found in U.S. Pat. No. 5,316,667, which is incorporated by reference.

F. The Optical Monitoring System

Figure 13:
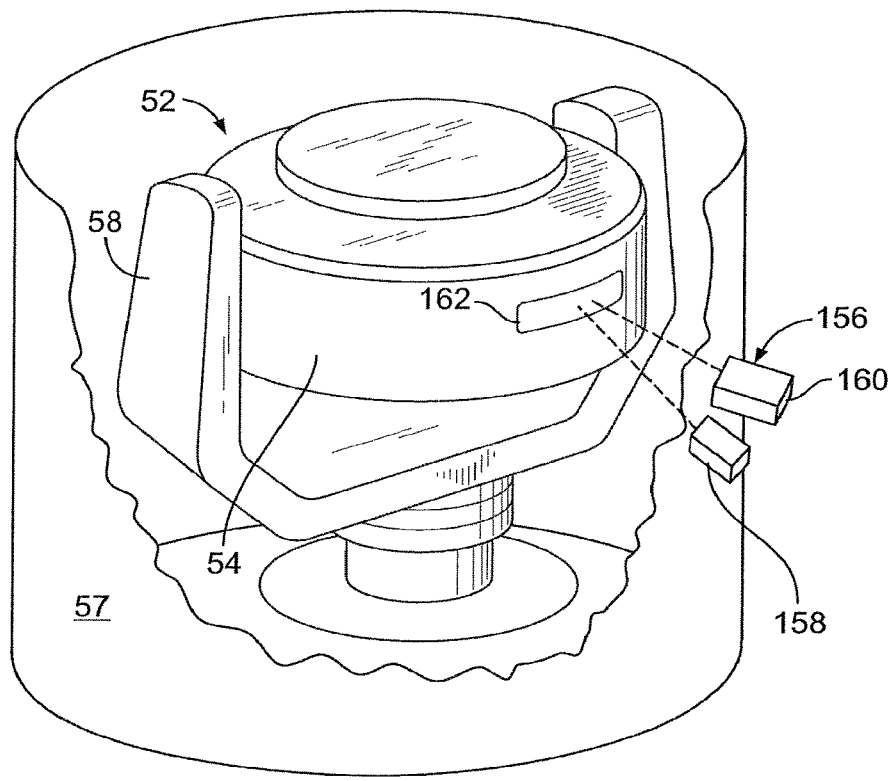
FIG. 13 is a side perspective view of the centrifuge, with a portion of the centrifuge bucket broken away to show the bowl and spool of the centrifuge in the operating position.

The separation device 10 includes an optical monitoring system 156 (FIG. 13) which is configured to directly monitor the disposable flow circuit 12 in the centrifuge 52. The illustrated monitoring system 156 includes a light source 158 and a light detector or image sensor 160. In the embodiment of FIG. 13, the monitoring system 156 is shown with one light source 158 and one light detector 160, but monitoring systems with a plurality of light source and/or a plurality of light detectors may also be employed without departing from the scope of the present disclosure. As will be described in greater detail herein, the monitoring system 156 may be configured to detect characteristics of flow through the flow circuit 12 (e.g., the location of the interface 150 on the ramp 152) and/or characteristics of the flow circuit 12 itself (such as, but not limited to, placement, positioning, and suitability of the circuit). The monitoring system 156 generates an output based on the images it observes and the output is used to control the flow of fluid through the flow circuit 12 (e.g., controlling flow to adjust the position of the interface 150 on the ramp 152) and/or whether a blood processing procedure will be initiated or continued.

Figure 14:
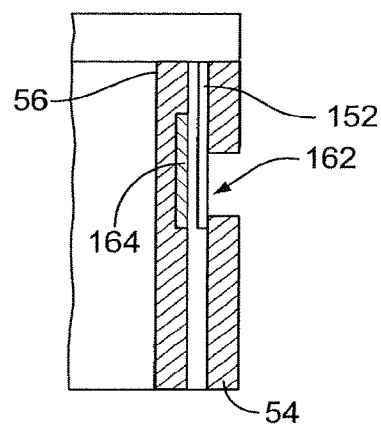
FIG. 14 is a side section view of the centrifuge bowl and spool of FIG. 13.

In one embodiment, the monitoring system 156 is positioned outside of the centrifuge 52. To allow the monitoring system 156 to directly monitor the blood separation chamber 34, the centrifuge bowl 54 may be transparent to the light emitted by the light source 158 in the region 162 where the bowl 54 overlies the interface ramp 152 (FIGS. 13 and 14). In the illustrated embodiment, the region 162 comprises a window cut out in the bowl 54. The remainder of the bowl 54 that lies in the path of the monitoring system 156 may be comprised of an opaque or light absorbing material.

In the illustrated embodiment, the monitoring system 156 is positioned outside of the centrifuge bucket 57 (FIG. 13). The yoke 58 rotates at a one omega speed as the spool 56 and bowl 54 rotate at a two omega speed. In embodiments where the monitoring system 156 is positioned outside of the centrifuge bucket 57, the light source 158 is stationary and does not rotate. Accordingly, the window 162 and ramp 152 will not always be in the field of view of the monitoring system 156. In one embodiment, the monitoring system 156 may be provided in an "always on" state, wherein all of the components and functionality employed during a monitoring state (i.e., the time when the blood separation chamber 34 is visible to the monitoring system 156 through the window 162) are employed and functional at all times during a blood separation procedure. For example, the light source 158 may be configured to continuously transmit light to the centrifuge 52, even when the window 162 (and, hence, the blood separation chamber 34) are not in the field of view of the monitoring system 156.

In other embodiments, the monitoring system 156 is provided with an electronic timing system for triggering full operation of the monitoring system 156 only when the blood separation chamber 34 (or an area of interest thereof) is visible to the monitoring system 156. The electronic timing system may include any of a variety of triggering mechanisms, including (but not limited to) an optical triggering mechanism, a mechanical triggering mechanism, and/or a magnetic triggering system. In one example of an optical triggering system, the window 162 and/or an area of interest of the blood separation chamber 34 is physically bounded at its leading and/or trailing edges by markers having a known intensity. When the monitoring system 156 detects a marker at the leading edge, it is an indication for the monitoring system 156 to become fully functional and initiate a monitoring state that is operative until a marker at the trailing edge has been detected, at which time the monitoring state may be deactivated. These markers may also serve as calibration features which act as a baseline against which any other detected light intensities are compared to account for variations in illumination and sensor sensitivity. In another embodiment, a direct drive system is employed and the position of the window 162 with respect to the monitoring system 156 is known in terms of the rotational location of the motor. In this case, the electronic timing system may function to turn the monitoring system 156 on and off depending on the rotational location of the motor.

Turning now to the light source 158 of the monitoring system 156, it is positioned and oriented to illuminate a portion of the flow circuit 12 received within the centrifuge 52 (i.e., the blood separation chamber 34). The light source 158 may be configured to continuously illuminate the blood separation chamber 34 during a monitoring state or may be intermittently operated (e.g., to provide stroboscopic illumination) during a monitoring state.

The light source 158 may be variously configured without departing from the scope of the present disclosure. For example, the light source 158 may include at least one light emitting diode, but may alternatively (or additionally) include any other suitable source of light. In general, a source of light would be considered suitable if it is capable of transmitting enough light to the blood separation chamber 34 that the light detector 160 will be able to detect an image thereof.

The monitoring system 156 is not limited to one light source 158, but may include a plurality of light sources. If the monitoring system 156 includes a plurality of light sources, the lights produced may have different wavelengths. The light sources may be operated simultaneously or independently of each other (e.g., sequentially).

The light detector 160 (FIG. 13) is configured to receive an image of the blood separation chamber 34, which may include both the blood separation chamber 34 itself, as well as the flow of fluid therethrough. As used in this context, the term "image" is to be broadly construed to refer to the light received by the light detector 160, and may include one- or two-dimensional distributions of light. The light detector 160 may be variously configured without departing from the scope of the present disclosure. For example, the light detector 160 may be provided as a linear array-type sensor (e.g., a charge-coupled device or photodiode array) which is configured to receive a one-dimensional image of the blood separation chamber 34. In another embodiment, the light detector 160 is instead provided as a two-dimensional array sensor and is configured to receive a two-dimensional image of the blood separation chamber 34. The light detector 160 may be otherwise configured without departing from the scope of the present disclosure. As described above, the area of interest of the centrifuge 52 (i.e., the transparent window 162 in the illustrated embodiment) may not be stationary with respect to the monitoring system 156, in which case it may be advantageous for the scan rate of the light detector 160 to be coupled to the rotational speed of the centrifuge 52 such that the same area of the blood separation chamber 34 is always scanned by the light detector 160. The monitoring system 156 is not limited to one light detector 160, but may include a plurality of light detectors.

In an exemplary procedure, the monitoring system 156 may be configured to determine the location of the interface 150 on the ramp 152 and (if necessary) adjust the flow of fluid through the blood separation chamber 34 to move the interface 150 to a target location on the ramp 152. In such an embodiment, the interface ramp 152 may be made of a light transmissive material such that, when the window 162 is in the field of view of the monitoring system 156, light from the light source 158 will pass through the window 162 of the bowl 54 and the ramp 152. The spool 56 may carry a light reflective material 164 (FIG. 14) behind the interface ramp 152 to enhance its reflective properties. The light reflective material 164 of the spool 56 reflects incoming light received from the light source 158 out through the window 162 of the bowl 54, where it is detected by the light detector 160 to form an image. The light detector 160 may detect a plurality of images during a single monitoring state or revolution of the centrifuge 52. The monitoring system 156 may include a focusing lens and/or reflectors with which light returning from the centrifuge 52 interacts prior to receipt by the light detector 160.

The monitoring system 156 also includes a controller, which may be the central controller of the separation device 10 or may be a separate component that interacts with the central controller. The controller is configured to combine two or more of the images sequentially received or scanned by the light detector 160 and generate a two-dimensional output. The controller may employ any of a variety of digital image processing techniques, such as filtering, diffusion, and edge detection in order to extract information from the two-dimensional output/image. Compared to known one-dimensional systems, monitoring systems according to the present disclosure have improved resolution (including multi-megapixel images of the small ramp 152 and window 162 with proper optics) and signal-to-noise ratio. Further, the effect of any noise or distortion present at the area of interest analyzed by the system is reduced by considering multiple images, examining the entire length of (or at least a greater portion of) the interface 150, and generating a two-dimensional image/output. Also, it is possible to determine more information regarding the interface 150 (e.g., the thickness of the interface 150, whether the interface 150 is angled, particulate flux, etc.). Compared to known two-dimensional sensor systems, monitoring systems according to the present disclosure may employ an "always on" light source 158 and do not require precise strobing of a light source to capture the areas of interest. Additionally, monitoring systems according to the present disclosure may be less susceptible to image-smearing, which may be more prevalent in known two-dimensional sensor systems due to the combination of slow frame rate and fast centrifugal motion of the area of interest.

The controller uses the two-dimensional output to control the flow of fluid through the flow circuit 12. In particular, the controller transmits the two-dimensional output (which represents the location of the interface 150 on the ramp 152) to an interface command element or module. The command element may include a comparator, which compares the two-dimensional interface location output with a desired interface location to generate an error signal. The error signal may take a number of forms but, in one embodiment, is expressed in terms of a targeted red blood cell percentage value (i.e., the percentage of the ramp 152 which should be occupied by the RBC layer 142).

When the control value is expressed in terms of a targeted red blood cell percentage value, a positive error signal indicates that the RBC layer 142 on the ramp 152 is too large (as FIG. 11 shows). The interface command element generates a signal to adjust an operational parameter accordingly, such as by reducing the rate at which plasma is removed through the first outlet port 68 under action of one or more of the pumps 92. The interface 150 moves away from the constricted passage 154 toward the desired control position (as FIG. 10 shows), where the error signal is zero.

A negative error signal indicates that the RBC layer 142 on the ramp 152 is too small (as FIG. 12 shows). The interface command element generates a signal to adjust an operational parameter accordingly, such as by increasing the rate at which plasma is removed through the first outlet port 68. The interface 150 moves toward the constricted passage 154 to the desired control position (FIG. 10), where the error signal is again zero.

Alternatively, or in addition to determining the location of the interface 150, the controller may be configured to determine other characteristics of fluid flow through the blood separation chamber 34 based (at least in part) on the two-dimensional image/output. The flow characteristics determinable by the optical monitoring system 156 may depend, in part, on the nature of the light source 158 (e.g., the wavelength of the light produced by the light source 158) and the inclusion of additional associated components (e.g., filters). The blood separation chamber 34 and/or the centrifuge 52 may also be specially configured to enhance the functionality of the optical monitoring system 156 (e.g., by providing features which allow a single light detector 160 to have different views of the area of interest). For example, the controller may be configured to use the two-dimensional image/output it creates to determine turbulence in flow through the blood separation chamber 34. In another embodiment, the controller may be configured to determine particulate flow in the blood separation chamber 34. In yet another embodiment, the controller may be configured to determine absolute intensity of light in the blood separation chamber 34. In still another embodiment, the controller is configured to determine hemolysis of blood cells in the blood separation chamber 34. In another embodiment, the controller is configured to determine the hematocrit of blood in the blood separation chamber 34. In yet another embodiment, the controller is configured to determine cell type of blood cells in the blood separation chamber 34. In still another embodiment, the controller is configured to determine lipemia in blood in the blood separation chamber 34. The controller may be configured to simultaneously determine two or more of these characteristics. Once determined, one or more of these characteristics may be used in estimating the yield of a separated blood component, determining white blood cell contamination, or calculating any of a number of other values.

As described above, in one embodiment, the light detector 160 is provided as a two-dimensional array sensor. A similar result may be achieved with a linear array sensor in a scanning mode or a two-dimensional array sensor in a strobed, single-shot mode. A two-dimensional array sensor may also be used as a linear array sensor (e.g., by examining only a single row or column thereof), meaning that a monitoring system 156 having such an light detector 160 may have improved flexibility in allowing an operator or technician to choose between using the light detector 160 as either a linear or two-dimensional array sensor. If the light detector 160 is provided and used as a two-dimensional array sensor, it may be advantageous to operate the light source 160 in a stroboscopic illumination mode to reduce image-smearing and distortion.

Figure 15:
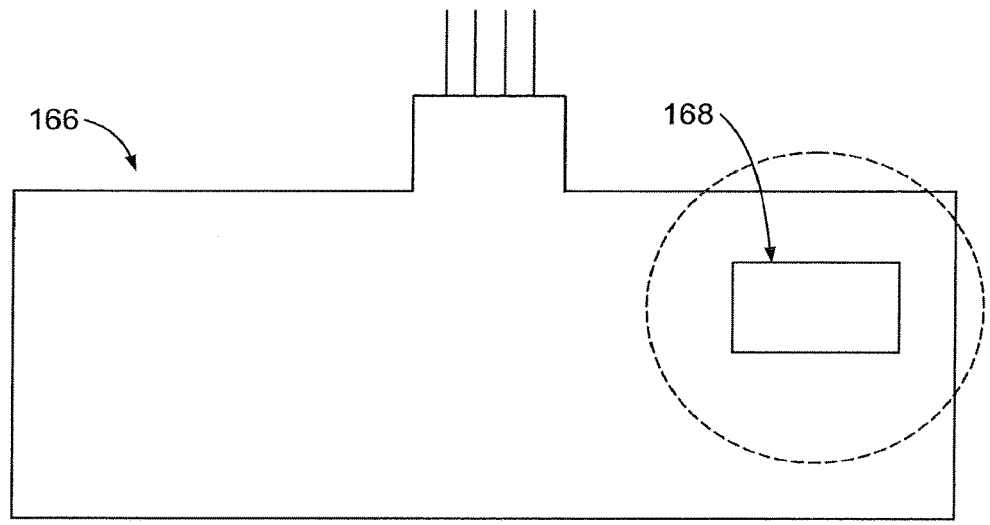
FIG. 15 is a diagrammatic view of a blood separation chamber incorporating an identification feature.
Figure 16:
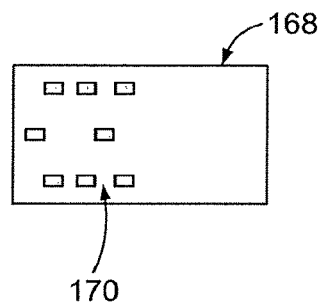
FIG. 16 is a detail view of the identification feature of FIG. 15.

In addition to determining characteristics of fluid flow, the monitoring system 156 may also be employed to determine characteristics of the flow circuit itself. Other optical monitoring systems, including suitably configured known and novel systems, may also be employed in connection with determining characteristics of the flow circuit itself, although it may be advantageous to employ optical monitoring systems according to the present disclosure for ease of extracting and analyzing information from received images. For example, FIG. 15 illustrates a blood separation chamber 166 of a flow circuit incorporating a region 168 with at least one identification feature 170 (FIG. 16). The identification feature 170 is configured to be detected by an optical monitoring system when the blood separation chamber 166 is received inside the centrifuge 52. The region 168 is positioned such that it is visible by an optical monitoring system. If the optical monitoring system is positioned outside of the centrifuge 52, the centrifuge bowl 54 may include an additional window or transparent region generally aligned with the region 168. Alternatively, the region 168 and the identification feature 170 may be positioned so as to overlay the ramp 152 and be visible through the above-described window 162 of the centrifuge bowl 54.

The optical monitoring system detects the presence (or lack thereof) of the identification feature 170 and then a controller associated with the monitoring system compares the detected identification feature to an expected identification feature. The expected identification feature corresponds to the identification feature of a blood separation chamber that is suitable for use with the separation device or for a particular blood processing operation carried out by the separation device. If the detected identification feature does not match the expected identification feature, it is an indication that the flow circuit is not approved for or suitable for use with the separation device 10. In this case, the controller may generate an alarm condition to alert an operator or technician that the flow circuit is not suitable and that the separation device will not initiate a blood separation procedure until the flow circuit has been replaced. On the other hand, if the detected identification feature does match the expected identification feature, it is an indication that the flow circuit is approved for or suitable for use with the separation device 10. In this case, the controller may initiate a blood separation procedure or otherwise allow the procedure to commence.

The identification feature 170 may be variously configured without departing from the scope of the present disclosure. In one embodiment, the identification feature 170 comprises a printed image, such as (but not limited to) a barcode. In another embodiment, the identification feature 170 comprises a portion of the blood separation chamber 166 having a material thickness different from the material thickness of the blood separation chamber 166 adjacent to the identification feature 170. In yet another embodiment, the identification feature 170 comprises a material contour different from a material contour of the blood separation chamber 166 adjacent to the identification feature 170. In another embodiment, the identification feature 170 comprises a region or second material having a different opacity from the opacity of the material of the blood separation chamber 166 adjacent to the identification feature 170. Any other optically detectable identification feature or a combination of different types of identification features may also be employed.

Figure 17:
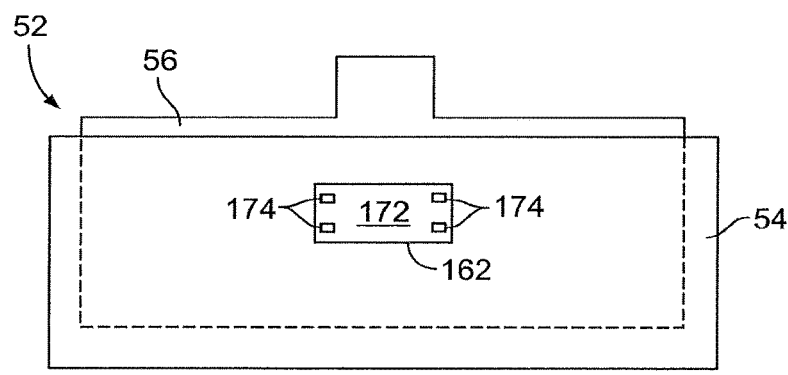
FIG. 17 is a diagrammatic view of a blood separation chamber incorporating an alignment feature and received within a centrifuge.

An optical monitoring system 156 according to the present disclosure (or any other suitable known or novel monitoring system) may also be employed to determine whether the flow circuit is properly aligned within the centrifuge 52. For example, FIG. 17 illustrates a blood separation chamber 172 of a flow circuit incorporating at least one alignment feature 174. The alignment feature 174 is configured to be detected by an optical monitoring system when the blood separation chamber 172 is received inside the centrifuge 52 (FIG. 17). If the optical monitoring system is positioned outside of the centrifuge 52, the centrifuge bowl 54 may include an additional window or transparent region generally aligned with the alignment feature 174. Alternatively, the alignment feature 174 may be positioned so as to overlay the ramp 152 and be visible through the above-described window 162 of the centrifuge bowl 54.

The optical monitoring system detects the presence (or lack thereof) of the alignment feature 174 and then a controller associated with the monitoring system compares the detected alignment feature to an expected alignment feature. This may include comparing the detected position of the alignment feature to an expected position of the alignment feature. The expected alignment feature corresponds to the alignment feature of a blood separation chamber that is properly aligned within the centrifuge 52 and that it is safe for a particular blood processing operation to be carried out by the separation device. If the detected alignment feature does not match the expected alignment feature, it is an indication that the flow circuit was not properly installed within the centrifuge 52. In this case, the controller may generate an alarm condition to alert an operator or technician that the flow circuit is not properly installed and that the separation device will not initiate a blood separation procedure until the flow circuit has been reinstalled. On the other hand, if the detected alignment feature does match the expected alignment feature, it is an indication that the flow circuit has been properly installed. In this case, the controller may initiate a blood separation procedure or otherwise allow the procedure to commence. The monitoring system may be configured to periodically monitor the alignment feature 174 and, if the detected alignment feature does not match the expected alignment feature (e.g., if the blood separation chamber 172 becomes misaligned during use of the separation device), the controller may generate an alarm condition and pause or terminate the procedure.

The alignment feature 174 may be variously configured without departing from the scope of the present disclosure. In the illustrated embodiment, the identification feature 174 comprises four markers arranged to be located adjacent to the four corners of the window 162 of the centrifuge bowl 54 when the blood separation chamber 172 is properly positioned within the centrifuge 52. If the four markers are not detected in their expected locations, it is an indication that the blood separation chamber 172 has been improperly installed.

As an alternative to employing optically detected alignment features, other means may be provided to ensure proper alignment of the blood separation chamber within the centrifuge. For example, the blood separation chamber and centrifuge may be provided with magnetic components or markers, requiring the proper alignment of the two for the magnetic components to be coupled together.

Aspects of the present subject matter described above may be beneficial alone or in combination with one or more other aspects. Without limiting the foregoing description, in accordance with one aspect of the subject matter herein, there is provided a disposable flow circuit for use in a blood processing system of the type including a centrifuge and an optical monitoring system. The circuit includes a blood separation chamber configured to be at least partially received inside the centrifuge for the flow of whole blood and/or a separated blood component therethrough. The circuit also includes an inlet tube for the flow of whole blood into the blood separation chamber and an outlet tube for the flow of a separated blood component out of the blood separation chamber. The blood separation chamber includes at least one identification feature configured to be detected by the monitoring system when the blood separation chamber is received inside the centrifuge to verify that the blood separation chamber is suitable for use with the centrifuge.

In accordance with another aspect which may be used or combined with the preceding aspect, the identification feature comprises a barcode.

In accordance with another aspect which may be used or combined with the first aspect, the identification feature comprises a printed image.

In accordance with another aspect which may be used or combined with the first aspect, the identification feature comprises a material thickness different from the material thickness of the blood separation chamber adjacent to said at least one identification feature.

In accordance with another aspect which may be used or combined with the first aspect, the identification feature comprises a material contour different from the material contour of the blood separation chamber adjacent to said at least one identification feature.

In accordance with another aspect which may be used or combined with the first aspect, the identification feature comprises an opacity different from the opacity of the blood separation chamber adjacent to said at least one identification feature.

In accordance with another aspect which may be used or combined with any of the preceding aspects, the blood separation chamber includes at least one alignment feature configured to be detected by the monitoring system when the blood separation chamber is received inside the centrifuge to verify that the blood separation chamber is properly aligned within the centrifuge.

In accordance with another aspect, there is provided a method of identifying a disposable flow circuit in a blood processing system. The method includes positioning at least a portion of a disposable flow circuit in a centrifuge and monitoring the disposable flow circuit to detect the presence of an expected identification feature. An alarm condition is generated if the expected identification feature is not detected, while a blood separation procedure is initiated if the expected identification feature is detected.

In accordance with another aspect which may be used or combined with the preceding aspect, the expected identification feature comprises a bar code.

In accordance with another aspect which may be used or combined with the eight aspect, the expected identification feature comprises a printed image.

In accordance with another aspect which may be used or combined with the eight aspect, the expected identification feature comprises a portion of the disposable flow circuit having a material thickness different from the material thickness of the disposable flow circuit adjacent to said portion.

In accordance with another aspect which may be used or combined with the eight aspect, the expected identification feature comprises a portion of the disposable flow circuit having a material contour different from a material contour of the disposable flow circuit adjacent to said portion.

In accordance with another aspect which may be used or combined with the eight aspect, the expected identification feature comprises a portion of the disposable flow circuit having an opacity different from the opacity of the disposable flow circuit adjacent to said portion.

In accordance with another aspect which may be used or combined with any of the preceding six aspects, monitoring the disposable flow circuit occurs through a window of the centrifuge.

In accordance with another aspect which may be used or combined with any of the preceding seven aspects, the method further comprises a step of monitoring the disposable flow circuit to detect the presence of an expected alignment feature. An alarm condition is generated if the expected identification feature or the alignment feature is not detected, while the blood separation procedure is carried out if the expected identification feature and the alignment feature are detected.

In accordance with another aspect, there is provided a disposable flow circuit for use in a blood processing system of the type including a centrifuge and an optical monitoring system. The circuit comprises a blood separation chamber configured to be at least partially received inside the centrifuge for the flow of whole blood and/or a separated blood component therethrough. The circuit also includes an inlet tube for the flow of whole blood into the blood separation chamber and an outlet tube for the flow of a separated blood component out of the blood separation chamber. The blood separation chamber includes at least one alignment feature configured to be detected by the monitoring system when the blood separation chamber is received inside the centrifuge to verify that the blood separation chamber is properly aligned within the centrifuge.

In accordance with another aspect, there is provided a method of identifying a disposable flow circuit in a blood processing system. The method includes positioning at least a portion of a disposable flow circuit in a centrifuge and monitoring the disposable flow circuit to detect the presence of an expected alignment feature. An alarm condition is generated if the expected alignment feature is not detected, while a blood separation procedure is initiated if the expected alignment feature is detected.

In accordance with another aspect which may be used or combined with the preceding aspect, monitoring the disposable flow circuit occurs through a window of the centrifuge.

In accordance with another aspect, there is provided a blood processing system. The system comprises a disposable flow circuit, a centrifuge, and a monitoring system. The disposable flow circuit is configured for the flow of whole blood and/or a separated blood component therethrough. The centrifuge is configured to receive at least a portion of the disposable flow circuit and separate at least one blood component from blood flowing through the disposable flow circuit. The monitoring system is configured to directly monitor the disposable flow circuit received by the centrifuge and includes a light source, a light detector, and a controller. The light source is configured to illuminate said at least a portion of the disposable flow circuit received by the centrifuge. The light detector is configured to receive an image of said at least a portion of the disposable flow circuit. The controller is configured to combine two or more of the images received by the light detector, generate a two-dimensional output, and control the separation of said at least one blood component from the blood in the disposable flow circuit based at least in part on said output.

In accordance with another aspect which may be used or combined with the preceding aspect, the light detector is configured to receive a one-dimensional image of said at least a portion of the disposable flow circuit.

In accordance with another aspect which may be used or combined with any of the preceding two aspects, the light detector comprises a linear array-type sensor.

In accordance with another aspect which may be used or combined with the nineteenth aspect, the light detector is configured to receive a two-dimensional image of said at least a portion of the disposable flow circuit.

In accordance with another aspect which may be used or combined with the nineteenth or twenty-second aspects, the light detector comprises a two-dimensional array sensor.

In accordance with another aspect which may be used or combined with any of the preceding five aspects, the controller is configured to determine the location of an interface between two separated blood components and move the interface toward a desired location within the disposable flow circuit.

In accordance with another aspect which may be used or combined with any of the preceding six aspects, the monitoring system is positioned outside of the centrifuge.

In accordance with another aspect which may be used or combined with any of the preceding seven aspects, the centrifuge includes a window through which the monitoring system directly monitors said at least a portion of the disposable flow circuit received by the centrifuge.

In accordance with another aspect which may be used or combined with any of the preceding eight aspects, a scan rate of the light detector is coupled to a rotational speed of the centrifuge.

In accordance with another aspect which may be used or combined with any of the preceding nine aspects, the controller is configured to determine turbulence in the disposable flow circuit.

In accordance with another aspect which may be used or combined with any of the preceding ten aspects, the controller is configured to determine particulate flow in the disposable flow circuit.

In accordance with another aspect which may be used or combined with any of the preceding eleven aspects, the controller is configured to determine absolute intensity of light in the disposable flow circuit.

In accordance with another aspect which may be used or combined with any of the preceding twelve aspects, the controller is configured to determine hemolysis of blood cells in the disposable flow circuit.

In accordance with another aspect which may be used or combined with any of the preceding thirteen aspects, the controller is configured to determine hematocrit of blood in the disposable flow circuit.

In accordance with another aspect which may be used or combined with any of the preceding fourteen aspects, the controller is configured to determine cell type of blood cells in the disposable flow circuit.

In accordance with another aspect which may be used or combined with any of the preceding fifteen aspects, the controller is configured to determine lipemia in blood in the disposable flow circuit.

In accordance with another aspect which may be used or combined with any of the preceding sixteen aspects, the disposable flow circuit includes at least one identification feature and the controller is configured to detect the presence of said at least one identification feature.

In accordance with another aspect which may be used or combined with any of the preceding seventeen aspects, the controller is configured to determine whether said at least a portion of the disposable flow circuit is properly aligned within the centrifuge.

In accordance with another aspect which may be used or combined with any of the preceding eighteen aspects, the light source is configured to continuously illuminate said at least a portion of the disposable flow circuit during a monitoring state.

In accordance with another aspect which may be used or combined with any of the preceding nineteen aspects, the system further comprises a plurality of light sources, wherein at least two of the light sources have different wavelengths.

In accordance with another aspect which may be used or combined with the preceding aspect, the plurality of light sources are configured to be operated sequentially.

In accordance with another aspect which may be used or combined with any of the preceding twenty-one aspects, the light source is configured to provide stroboscopic illumination to said at least a portion of the disposable flow circuit.

In accordance with another aspect which may be used or combined with any of the preceding twenty-two aspects, the light source includes an electronic timing system configured to selectively operate the light source when an area of interest of said at least a portion of the disposable flow circuit is in the field of view of the monitoring system.

In accordance with another aspect which may be used or combined with the preceding aspect, the electronic timing system includes an optical triggering mechanism.

In accordance with another aspect which may be used or combined with the forty-first aspect, the electronic timing system includes a mechanical triggering mechanism.

In accordance with another aspect which may be used or combined with the forty-first aspect, the electronic timing system includes a magnetic triggering mechanism.

In accordance with another aspect which may be used or combined with the forty-first aspect, the system further includes a motor, with the electronic timing system including a triggering mechanism based at least in part on the rotational location of the motor.

In accordance with another aspect which may be used or combined with any of the preceding twenty-seven aspects, the disposable flow circuit and/or the centrifuge includes a calibration marker positioned adjacent to an area of interest of said at least a portion of the disposable flow circuit.

In accordance with another aspect which may be used or combined with the preceding aspect, a monitoring state of the light detector is initiated upon detection of the calibration marker.

In accordance with another aspect which may be used or combined with any of the preceding two aspects, the calibration marker has a known brightness and the controller is configured to adjust the operation of the light source and/or the light detector based on a comparison of a detected brightness of the calibration marker to the known brightness.

In accordance with another aspect, there is provided a method of controlling a blood separation procedure. The method includes separating at least one blood component from blood in a centrifuge and applying light to the interior of the centrifuge. An image of the interior of the centrifuge is received and two or more of such images are combined. A two-dimensional output is generated based, at least in part, on said two or more of said images and the separation of said at least one blood component from the blood in the centrifuge is controlled based, at least in part, on said two-dimensional output.

In accordance with another aspect which may be used or combined with the preceding aspect, receiving an image includes receiving a one-dimensional image of the interior of the centrifuge.

In accordance with another aspect which may be used or combined with the forty-ninth aspect, receiving an image includes receiving a two-dimensional image of the interior of the centrifuge.

In accordance with another aspect which may be used or combined with any of the preceding three aspects, generating a two-dimensional output includes determining the location of an interface between two separated blood components and said controlling the separation includes moving the interface toward a desired location within the centrifuge.

In accordance with another aspect which may be used or combined with any of the preceding four aspects, applying light and receiving an image occur at a position outside of the centrifuge.

In accordance with another aspect which may be used or combined with any of the preceding five aspects, receiving an image occurs at a scan rate which is coupled to a rotational speed of the centrifuge.

In accordance with another aspect which may be used or combined with any of the preceding six aspects, generating a two-dimensional output includes determining turbulence in the centrifuge.

In accordance with another aspect which may be used or combined with any of the preceding seven aspects, generating a two-dimensional output includes determining particulate flow in the centrifuge.

In accordance with another aspect which may be used or combined with any of the preceding eight aspects, generating a two-dimensional output includes determining absolute intensity of light in the centrifuge.

In accordance with another aspect which may be used or combined with any of the preceding nine aspects, generating a two-dimensional output includes determining hemolysis of blood cells in the centrifuge.

In accordance with another aspect which may be used or combined with any of the preceding ten aspects, generating a two-dimensional output includes determining hematocrit of blood in the centrifuge.

In accordance with another aspect which may be used or combined with any of the preceding eleven aspects, generating a two-dimensional output includes determining cell type of blood cells in the centrifuge.

In accordance with another aspect which may be used or combined with any of the preceding twelve aspects, generating a two-dimensional output includes determining lipemia in blood in the centrifuge.

In accordance with another aspect which may be used or combined with any of the preceding thirteen aspects, separating at least one blood component includes separating at least one blood component in blood in a disposable flow circuit at least partially received inside of the centrifuge, and generating a two-dimensional output includes detecting the presence of at least one identification feature of the disposable flow circuit.

In accordance with another aspect which may be used or combined with any of the preceding fourteen aspects, separating at least one blood component includes separating at least one blood component in blood in a disposable flow circuit at least partially received inside of the centrifuge, and generating a two-dimensional output includes determining whether the disposable flow circuit is properly aligned within the centrifuge.

In accordance with another aspect which may be used or combined with any of the preceding fifteen aspects, applying light includes applying a plurality of lights having different wavelengths.

In accordance with another aspect which may be used or combined with the preceding aspect, applying light includes operating the lights sequentially.

In accordance with another aspect which may be used or combined with any of the preceding seventeen aspects, applying light includes providing stroboscopic illumination to the centrifuge.

In accordance with another aspect which may be used or combined with any of the preceding eighteen aspects, applying light includes continuously applying light to the centrifuge during a monitoring state.

In accordance with another aspect which may be used or combined with any of the preceding nineteen aspects, applying light includes selectively applying light when an area of interest of the centrifuge is in the field of view of the light.

In accordance with another aspect which may be used or combined with the preceding aspect, applying light is optically triggered.

In accordance with another aspect which may be used or combined with the sixty-eighth aspect, said applying light is mechanically triggered.

In accordance with another aspect which may be used or combined with the sixty-eighth aspect, said applying light is magnetically triggered.

In accordance with another aspect which may be used or combined with the sixty-eighth aspect, applying light is triggered based at least in part on the rotational location of a motor.

In accordance with another aspect which may be used or combined with any of the preceding twenty-four aspects, separating at least one blood component includes separating at least one blood component in blood in a disposable flow circuit at least partially received in the centrifuge. The disposable flow circuit and/or the centrifuge includes a calibration marker positioned adjacent to an area of interest of the disposable flow circuit, and a monitoring state is initiated upon detection of the calibration marker.

In accordance with another aspect, there is provided a blood processing system comprising a centrifuge bucket, a centrifuge, and a monitoring system. The centrifuge is positionable within the centrifuge bucket and configured to receive at least a portion of a disposable flow circuit to separate at least one blood component from blood flowing through the disposable flow circuit. The monitoring system is configured to directly monitor a disposable flow circuit received by the centrifuge when the centrifuge is positioned within the centrifuge bucket, wherein the monitoring system is positioned outside of the centrifuge bucket.

In accordance with another aspect which may be used or combined with the preceding aspect, the centrifuge includes a window through which the monitoring system directly monitors a disposable flow circuit received by the centrifuge.

In accordance with another aspect which may be used or combined with any of the preceding two aspects, the monitoring system comprises a light source and a light detector. The light source is configured to illuminate a disposable flow circuit received by the centrifuge. The light detector is configured to receive an image of the disposable flow circuit.

In accordance with another aspect which may be used or combined with the preceding aspect, the light detector is configured to receive a one-dimensional image of a disposable flow circuit received by the centrifuge.

In accordance with another aspect which may be used or combined with any of the preceding two aspects, the light detector comprises a linear array-type sensor.

In accordance with another aspect which may be used or combined with the seventy-sixth aspect, the light detector is configured to receive a two-dimensional image of a disposable flow circuit received by the centrifuge.

In accordance with another aspect which may be used or combined with the seventy-sixth or the preceding aspect, the light detector comprises a two-dimensional array sensor.

In accordance with another aspect which may be used or combined with any of the preceding five aspects, a scan rate of the light detector is coupled to a rotational speed of the centrifuge.

In accordance with another aspect which may be used or combined with any of the preceding six aspects, the light source is configured to continuously illuminate a disposable flow circuit received by the centrifuge during a monitoring state.

In accordance with another aspect which may be used or combined with any of the preceding seven aspects, the system includes a plurality of light sources, wherein at least two of the light sources have different wavelengths.

In accordance with another aspect which may be used or combined with the preceding aspect, the plurality of light sources are configured to be operated sequentially.

In accordance with another aspect which may be used or combined with any of the preceding nine aspects, the light source is configured to provide stroboscopic illumination to a disposable flow circuit received by the centrifuge.

In accordance with another aspect which may be used or combined with any of the preceding ten aspects, the light source includes an electronic timing system configured to selectively operate the light source when an area of interest of a disposable flow circuit received by the centrifuge is in the field of view of the monitoring system.

In accordance with another aspect which may be used or combined with the preceding aspect, the electronic timing system includes an optical triggering mechanism.

In accordance with another aspect which may be used or combined with the eighty-sixth aspect, the electronic timing system includes a mechanical triggering mechanism.

In accordance with another aspect which may be used or combined with the eighty-sixth aspect, the electronic timing system includes a magnetic triggering mechanism.

In accordance with another aspect which may be used or combined with the eighty-sixth aspect, the system includes a motor, wherein the electronic timing system includes a triggering mechanism based at least in part on the rotational location of the motor.

In accordance with another aspect which may be used or combined with any of the preceding fifteen aspects, the system includes a controller configured to combine two or more of the images received by the light detector and generate a two-dimensional output used for controlling the separation of said at least one blood component from the blood in a disposable flow circuit received by the centrifuge.

In accordance with another aspect which may be used or combined with the preceding aspect, the controller is configured to determine turbulence in a disposable flow circuit received by the centrifuge.

In accordance with another aspect which may be used or combined with any of the preceding two aspects, the controller is configured to determine particulate flow in a disposable flow circuit received by the centrifuge.

In accordance with another aspect which may be used or combined with any of the preceding three aspects, the controller is configured to determine absolute intensity of light in a disposable flow circuit received by the centrifuge.

In accordance with another aspect which may be used or combined with any of the preceding four aspects, the controller is configured to determine hemolysis of blood cells in a disposable flow circuit received by the centrifuge.

In accordance with another aspect which may be used or combined with any of the preceding five aspects, the controller is configured to determine hematocrit of blood in a disposable flow circuit received by the centrifuge.

In accordance with another aspect which may be used or combined with any of the preceding six aspects, the controller is configured to determine cell type of blood cells in a disposable flow circuit received by the centrifuge.

In accordance with another aspect which may be used or combined with any of the preceding seven aspects, the controller is configured to determine lipemia in blood in a disposable flow circuit received by the centrifuge.

In accordance with another aspect which may be used or combined with any of the preceding eight aspects, the system includes a disposable flow circuit configured to be at least partially received by the centrifuge, wherein the controller is configured to determine whether the disposable flow circuit is properly aligned within the centrifuge.

In accordance with another aspect which may be used or combined with any of the preceding nine aspects, the system includes a disposable flow circuit configured to be at least partially received by the centrifuge, wherein the disposable flow circuit includes at least one identification feature and the controller is configured to detect the presence of said at least one identification feature.

In accordance with another aspect which may be used or combined with the preceding aspect, the identification feature comprises a barcode.

In accordance with another aspect which may be used or combined with the one hundredth aspect, the identification feature comprises a printed image.

In accordance with another aspect which may be used or combined with the one hundredth aspect, the identification feature comprises a material thickness different from the material thickness of the disposable flow circuit adjacent to said at least one identification feature.

In accordance with another aspect which may be used or combined with the one hundredth aspect, the identification feature comprises a material contour different from the material contour of the disposable flow circuit adjacent to said at least one identification feature.

In accordance with another aspect which may be used or combined with the one hundredth aspect, the identification feature comprises an opacity different from the opacity of the disposable flow circuit adjacent to said at least one identification feature.

In accordance with another aspect which may be used or combined with any of the preceding fifteen aspects, the controller is configured to determine the location of an interface between two separated blood components and move the interface toward a desired location within a disposable flow circuit received by the centrifuge.

In accordance with another aspect which may be used or combined with any of the preceding sixteen aspects, the system includes a disposable flow circuit configured to be at least partially received by the centrifuge, wherein the disposable flow circuit and/or the centrifuge includes a calibration marker positioned adjacent to an area of interest of the disposable flow circuit.

In accordance with another aspect which may be used or combined with the preceding aspect, a monitoring state of the light detector is initiated upon detection of the calibration marker.

In accordance with another aspect which may be used or combined with any of the preceding two aspects, the calibration marker has a known brightness and the controller is configured to adjust the operation of the light source and/or the light detector based on a comparison of a detected brightness of the calibration marker to the known brightness.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood processing system, comprising:
   a disposable flow circuit configured for the flow of whole blood and/or a separated blood component therethrough;
   a centrifuge configured to receive at least a portion of the disposable flow circuit and rotate about a rotational axis to separate at least one blood component from blood flowing through the disposable flow circuit; and
   a monitoring system configured to directly monitor the disposable flow circuit received by the centrifuge and comprising
      a light source configured to illuminate said at least a portion of the disposable flow circuit received by the centrifuge,
      a plurality of light detectors each configured to receive an image of said at least a portion of the disposable flow circuit, and
      a controller configured to combine two or more of the images received by the plurality of light detectors, generate a two-dimensional output, and control the separation of said at least one blood component from the blood in the disposable flow circuit based at least in part on said output, wherein
      the monitoring system is configured to cause the light source to continuously illuminate said at least a portion of the disposable flow circuit during separation of said at least one blood component from the blood in the disposable flow circuit,
      the plurality of light detectors comprise photodiodes incorporated into a linear array-type sensor and positioned at different locations in a direction parallel to the rotational axis, and
      the two or more images are sequentially received by adjacent light detectors before being combined by the controller.

2. The blood processing system of claim 1, wherein each one of the plurality of light detectors is configured to receive a one-dimensional image of said at least a portion of the disposable flow circuit.

3. The blood processing system of claim 1, wherein the controller is configured to determine the location of an interface between two separated blood components and move the interface toward a desired location within the disposable flow circuit.

4. The blood processing system of claim 1, wherein the controller is configured to determine at least one of: turbulence, particulate flow, absolute intensity of light, hemolysis of blood cells, hematocrit of blood, cell type of blood cells, and lipemia in blood in the disposable flow circuit.

5. The blood processing system of claim 3, wherein the controller is configured to examine an entire length of the interface.

6. The blood processing system of claim 3, wherein the controller is configured to determine a thickness of the interface.

7. The blood processing system of claim 3, wherein the controller is configured to determine whether the interface is angled.

8. The blood processing system of claim 1, wherein the controller is configured to simultaneously determine at least two of: turbulence, particulate flow, absolute intensity of light, hemolysis of blood cells, hematocrit of blood, cell type of blood cells, and lipemia in blood in the disposable flow circuit.

* * * * *